United States Patent
Lian et al.

(10) Patent No.: US 9,211,414 B2
(45) Date of Patent: Dec. 15, 2015

(54) IMPLANTABLE HEART STIMULATOR AND METHOD FOR TRENDING ANALYSIS OF VENTRICULAR ACTIVATION TIME

(75) Inventors: Jie Lian, Beaverton, OR (US); Dirk Muessig, West Linn, OR (US)

(73) Assignee: BIOTRONIK SE & CO KG (DE)

( * ) Notice: Subject to any disclaimer, the term of this patent is extended or adjusted under 35 U.S.C. 154(b) by 636 days.

(21) Appl. No.: 13/449,345

(22) Filed: Apr. 18, 2012

(65) Prior Publication Data

US 2012/0290027 A1 Nov. 15, 2012

Related U.S. Application Data

(60) Provisional application No. 61/485,133, filed on May 12, 2011.

(51) Int. Cl.
| | |
|---|---|
| *A61N 1/00* | (2006.01) |
| *A61N 1/365* | (2006.01) |
| *A61B 5/00* | (2006.01) |
| *A61B 5/042* | (2006.01) |
| *A61B 5/0452* | (2006.01) |
| *A61N 1/368* | (2006.01) |
| *A61B 5/0472* | (2006.01) |
| *A61N 1/362* | (2006.01) |

(52) U.S. Cl.
CPC .......... *A61N 1/36507* (2013.01); *A61B 5/0031* (2013.01); *A61B 5/042* (2013.01); *A61B 5/0452* (2013.01); *A61B 5/7275* (2013.01); *A61N 1/368* (2013.01); *A61B 5/0472* (2013.01); *A61N 1/3627* (2013.01)

(58) Field of Classification Search
CPC ...... A61N 1/39; A61N 1/3925; A61N 1/3993

USPC ......................................................... 607/5/4
See application file for complete search history.

(56) References Cited

U.S. PATENT DOCUMENTS

| | | | |
|---|---|---|---|
| 6,424,865 B1 | 7/2002 | Ding | |
| 7,532,929 B2 | 5/2009 | Mussig et al. | |
| 7,580,748 B2 | 8/2009 | Garner et al. | |
| 7,583,996 B2 | 9/2009 | Lian et al. | |
| 7,603,172 B2 | 10/2009 | Lian et al. | |
| 7,693,575 B2 | 4/2010 | Muessig et al. | |
| 7,761,163 B2 | 7/2010 | De Voir et al. | |

(Continued)

OTHER PUBLICATIONS

European Search Report, Appln. No. 12166541.8-2305, Sep. 17, 2012.

*Primary Examiner* — Christopher D Koharski
*Assistant Examiner* — Philip Edwards
(74) *Attorney, Agent, or Firm* — Craig A. Fieschko, Esq.; DeWitt Ross & Stevens S.C.

(57) ABSTRACT

Exemplary versions of the invention include methods and apparatuses for assessing ventricular activation time by determining a point in time t1 of an initial positive deflection on a far-field electrogram and a point in time t2 of a first peak of the negative deflection on a near-field electrogram of a same heart cycle. They also determine a time difference between points in time t1 and t2 said time difference representing the ventricular activation time. A progression of ventricular conduction disorders such as the left bundle branch block (LBBB) and the right bundle branch block (RBBB) can be monitored. Trending analysis of the ventricular activation time provides a means for monitoring the progression of ventricular conduction diseases.

20 Claims, 5 Drawing Sheets

(56) References Cited

U.S. PATENT DOCUMENTS

| | | |
|---|---|---|
| 7,822,475 B2 | 10/2010 | Schomburg et al. |
| 7,835,792 B2 | 11/2010 | Lian et al. |
| 7,899,520 B2 | 3/2011 | Lian et al. |
| 7,970,462 B2 | 6/2011 | Lefkov et al. |
| 7,985,185 B2 | 7/2011 | De Voir et al. |
| 8,019,406 B2 | 9/2011 | Lian et al. |
| 8,019,407 B2 | 9/2011 | Lian et al. |
| 8,024,031 B2 | 9/2011 | Nigam et al. |
| 8,060,198 B2 | 11/2011 | Lian et al. |
| 8,064,998 B2 | 11/2011 | Good et al. |
| 8,082,028 B2 | 12/2011 | Lian et al. |
| 8,090,434 B2 | 1/2012 | Lian et al. |
| 2002/0062139 A1 | 5/2002 | Ding |
| 2003/0009199 A1 | 1/2003 | Reinke et al. |
| 2003/0023175 A1* | 1/2003 | Arzbaecher et al. .......... 600/509 |
| 2004/0122479 A1* | 6/2004 | Spinelli et al. ................. 607/27 |
| 2005/0038480 A1 | 2/2005 | Ding |
| 2005/0165455 A1 | 7/2005 | Schomburg et al. |
| 2005/0187585 A1 | 8/2005 | Mussig et al. |
| 2007/0088401 A1 | 4/2007 | Spinelli et al. |
| 2007/0265539 A1 | 11/2007 | Hastings et al. |
| 2007/0265667 A1 | 11/2007 | Muessig et al. |
| 2007/0265670 A1 | 11/2007 | Lang et al. |
| 2007/0288063 A1 | 12/2007 | De Voir et al. |
| 2008/0065161 A1 | 3/2008 | Lian et al. |
| 2008/0114409 A1 | 5/2008 | Lian et al. |
| 2008/0114411 A1 | 5/2008 | Lian et al. |
| 2008/0125822 A1 | 5/2008 | Muessig et al. |
| 2008/0125823 A1 | 5/2008 | Muessig et al. |
| 2008/0125824 A1* | 5/2008 | Sauer et al. ...................... 607/14 |
| 2008/0140146 A1 | 6/2008 | Garner et al. |
| 2008/0154318 A1 | 6/2008 | Albus et al. |
| 2008/0177344 A1* | 7/2008 | Maskara et al. ................ 607/25 |
| 2008/0183088 A1 | 7/2008 | Lian et al. |
| 2008/0269826 A1 | 10/2008 | Lian et al. |
| 2008/0281369 A1 | 11/2008 | KenKnight et al. |
| 2008/0294217 A1 | 11/2008 | Lian et al. |
| 2008/0300504 A1 | 12/2008 | Lefkov et al. |
| 2009/0088814 A1 | 4/2009 | Good et al. |
| 2009/0125077 A1 | 5/2009 | Doerr et al. |
| 2009/0228061 A1 | 9/2009 | Lian et al. |
| 2009/0240157 A1 | 9/2009 | Lian et al. |
| 2009/0240298 A1 | 9/2009 | Lian et al. |
| 2009/0240300 A1 | 9/2009 | Lian et al. |
| 2009/0299203 A1 | 12/2009 | De Voir et al. |
| 2009/0312649 A1 | 12/2009 | Lian et al. |
| 2010/0099995 A1 | 4/2010 | Lian et al. |
| 2010/0099996 A1 | 4/2010 | Nigam et al. |
| 2010/0100143 A1 | 4/2010 | Nigam et al. |
| 2010/0106033 A1 | 4/2010 | Lian et al. |
| 2010/0217143 A1 | 8/2010 | Whittington et al. |
| 2010/0292596 A1 | 11/2010 | Moulder et al. |
| 2011/0130669 A1 | 6/2011 | Garner et al. |
| 2011/0218449 A1 | 9/2011 | Sauer et al. |
| 2011/0263987 A1 | 10/2011 | Lian et al. |
| 2012/0016249 A1 | 1/2012 | Lian et al. |

* cited by examiner

IMPLANTABLE HEART STIMULATOR AND METHOD FOR TRENDING ANALYSIS OF VENTRICULAR ACTIVATION TIME

CROSS-REFERENCE TO RELATED APPLICATIONS

This application claims priority under 35 USC §119(e) to U.S. Provisional Patent Application 61/485,133 filed May 12, 2011, the entirety of which is incorporated by reference herein.

FIELD OF THE INVENTION

The present invention relates to an implantable heart stimulator such as dual-chamber (RA-RV), three-chamber (BiA-RV, or RA-BiV), or four-chamber (BiA-BiV) implantable cardiac devices including pacemakers, defibrillators and cardiovertors, which stimulate cardiac tissue electrically to control a patient's heart rhythm.

BACKGROUND OF THE INVENTION

It is an object of exemplary versions of the invention to provide an apparatus and a method for monitoring a progression of ventricular conduction disorders such as the left bundle branch block (LBBB) and the right bundle branch block (RBBB).

There is no existing solution on continuous monitoring of the progression of LBBB/RBBB.

LBBB and RBBB are mainly diagnosed based on examination of the QRS morphology in surface ECG.

Implantable pacemakers and defibrillators traditionally measure the conduction time from atrial event (paced or sensed) to (sensed) ventricular event.

Continuous evaluation of QRS morphology for monitoring the progression of LBBB/RBBB is technically challenging, and there is no established method to quantify the QRS morphology variation as an indicator of ventricular conduction abnormality.

The atrium-ventricle conduction time measured by traditional implantable devices is the lumped sum of atrial conduction time, AV nodal conduction time, and the ventricular conduction time. Therefore, it is difficult to isolate the ventricular conduction time and analyze its change over time.

SUMMARY OF THE INVENTION

The object mentioned supra is achieved by an exemplary apparatus and method for trending analysis of the ventricular activation time as a means to monitor the progression of ventricular conduction diseases.

An exemplary implantable heart stimulator includes a housing and electronic circuitry, wherein the housing encloses the electronic circuitry and has an at least partially electrically conducting outer surface. The electronic circuitry is connected or can be connected to at least one electrode lead that carries at least two electrodes. The electronic circuitry includes a far-field electrogram recording unit that is electrically connected or can be connected to the at least partially electrically conducting outer surface and to a first one of the at least two electrodes. The electronic circuitry additionally includes a near-field electrogram recording unit that is electrically connected or can be connected to at least two electrodes carried by the electrode lead. The electronic circuitry further includes a ventricular activation time assessing unit that is operatively connected to the far-field electrogram recording unit and the near-field electrogram recording unit. The ventricular activation time assessing unit is configured to determine a point in time t1 of an initial positive deflection on a far-field electrogram and a point in time t2 of a first peak of the negative deflection on a near-field electrogram of a same heart cycle. The ventricular activation time assessing unit is further configured to determine a time difference between points in time t1 and t2, wherein this time difference represents the ventricular activation time.

An exemplary method for assessing a ventricular activation time is includes the step of determining a point in time t1 of an initial positive deflection on a far-field electrogram and a point in time t2 of a first peak of the negative deflection on a near-field electrogram of a same heart cycle. The method further includes the step of determining a time difference between points in time t1 and t2, wherein the time difference represents the ventricular activation time.

Exemplary versions of the invention recognize that the ventricular activation time (VAT) can be derived from simultaneous recording of near-field and far-field ventricular electrograms. The VAT measures the time difference from the onset of the QRS complex in the far-field electrogram to the intrinsic deflection of the near-field electrogram. Prolonged VAT measured in the left ventricle may reflect the progression of the left bundle branch block (LBBB), and prolonged VAT measured in the right ventricle may reflect the progression of the right bundle branch block (RBBB). Trending analysis of VAT can thus provide diagnosis of LBBB/RBBB and may predict imminent myocardial ischemia.

Regarding the implantable heart stimulator, it is preferred that the first electrode is a defibrillation electrode. It is further preferred that the electrode lead is a ventricular electrode lead. Preferably, the near-field electrogram recording unit is a ventricular sensing unit.

According to a preferred version, the heart stimulator is configured to repeatedly measure the ventricular activation time in a right ventricle and/or a left ventricle after each ventricular sensed event.

Preferably, the heart stimulator is configured to continuously measure the ventricular activation time periodically or at predefined time of the day when ventricular senses are encouraged to occur. The occurrence of ventricular senses corresponding to intrinsic (natural) contractions of a ventricle can be promoted by prolonging a corresponding ventricular escape interval. The ventricular escape interval is timed by the implantable heart stimulator if the implantable heart stimulator is operated in a demand mode in which a ventricular stimulation pulse is triggered at the end of a ventricular escape interval unless a natural contraction of the ventricle (a ventricular sense event) occurs prior to time out of the ventricular escape interval.

The implantable heart stimulator preferably includes a device memory and is configured to store measured ventricular activation times in the device memory in such a way that they can be used for trending analysis.

Optionally, a ventricular activation time trend analyzing unit can be directly or indirectly connected to the ventricular activation time assessing unit. The ventricular activation time trend analyzing unit is configured to analyze a trend in ventricular activation time by comparing most recently measured ventricular activation time values with a moving average of the previously measured ventricular activation time values. The ventricular activation time trend analyzing unit is further configured to trigger a warning signal when an increase in ventricular activation time values exceeding a predefined threshold is detected.

The implantable heart stimulator preferably further includes a telemetry unit and is configured to transmit stored ventricular activation time values and/or ventricular activation time trend data to a remote service center.

The implantable heart stimulator may also optionally be configured to transmit ventricular activation time trend data at a predetermined time of day or a predetermined time interval.

Further, the implantable heart stimulator can be configured to transmit ventricular activation time trend data to a remote service center upon device detection of a sudden increase of ventricular activation time that exceeds a predefined threshold. The predefined threshold can be either an absolute time interval or a percentage of a previous ventricular activation time average.

It is preferred that the exemplary method includes repeated measurement of ventricular activation time in a right ventricle and/or a left ventricle after each ventricular sensed event.

The exemplary method preferably also includes the step of storing measured ventricular activation time values in such way that they can be used for trending analysis.

The method preferably includes the step of analyzing a trend in ventricular activation time by comparing most recently measured ventricular activation time values with a moving average of the previously measured ventricular activation time values. A warning signal can be triggered when an increase in ventricular activation time values is detected that exceeds a predefined threshold.

The method also preferably includes the step of transmitting ventricular activation time trend data to a remote service center upon detection of a sudden increase of ventricular activation time that exceeds a predefined threshold. The predefined threshold may be either an absolute time interval or a percentage of previous ventricular activation time average.

BRIEF DESCRIPTION OF THE DRAWINGS

The foregoing and other objectives, advantages and novel features of the present invention can be understood and appreciated by reference to the following detailed description of exemplary versions of the invention, taken in conjunction the accompanying drawings, in which.

DETAILED DESCRIPTION OF PREFERRED VERSIONS OF THE INVENTION

Figure 1:
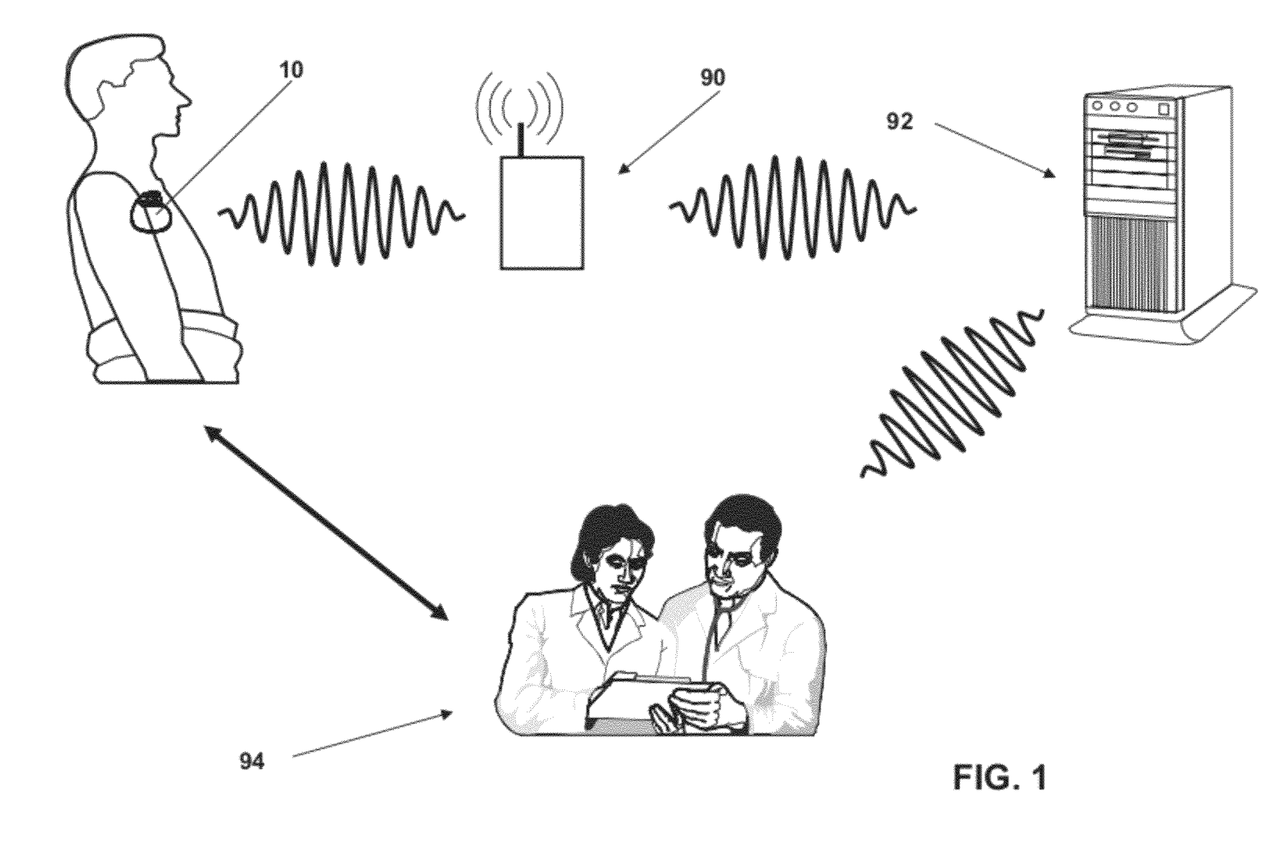
FIG. 1 is an overview of an exemplary patient monitoring system including an implantable heart stimulator.

In FIG. 1, a remote monitoring system including an implantable heart stimulator 10, an external device 90 and a central data server 92 of a central service center is displayed. Such a system allows data communication between the implantable heart stimulator 10 and the central server 92 via the external device 90. The external device 90 is configured to communicate wirelessly with the implantable heart stimulator 10.

Figure 2:
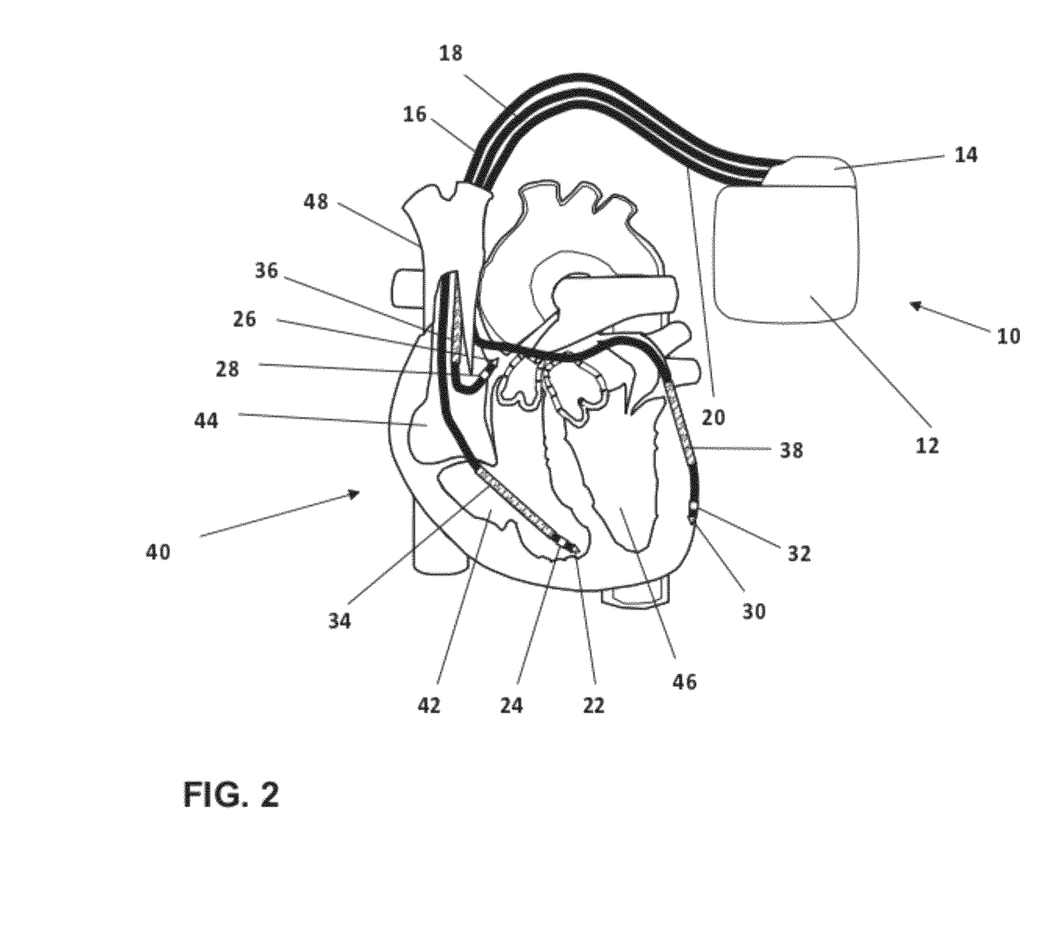
FIG. 2 illustrates an exemplary heart stimulator connected to electrode leads that are placed in a heart.

The stimulator 10 in FIG. 2 includes a housing or case 12 and a header 14.

The heart stimulator 10 is connected to three electrode leads, namely a right ventricular electrode lead 16, a right atrial electrode lead 18 and a left ventricular electrode lead 20.

Figure 3:
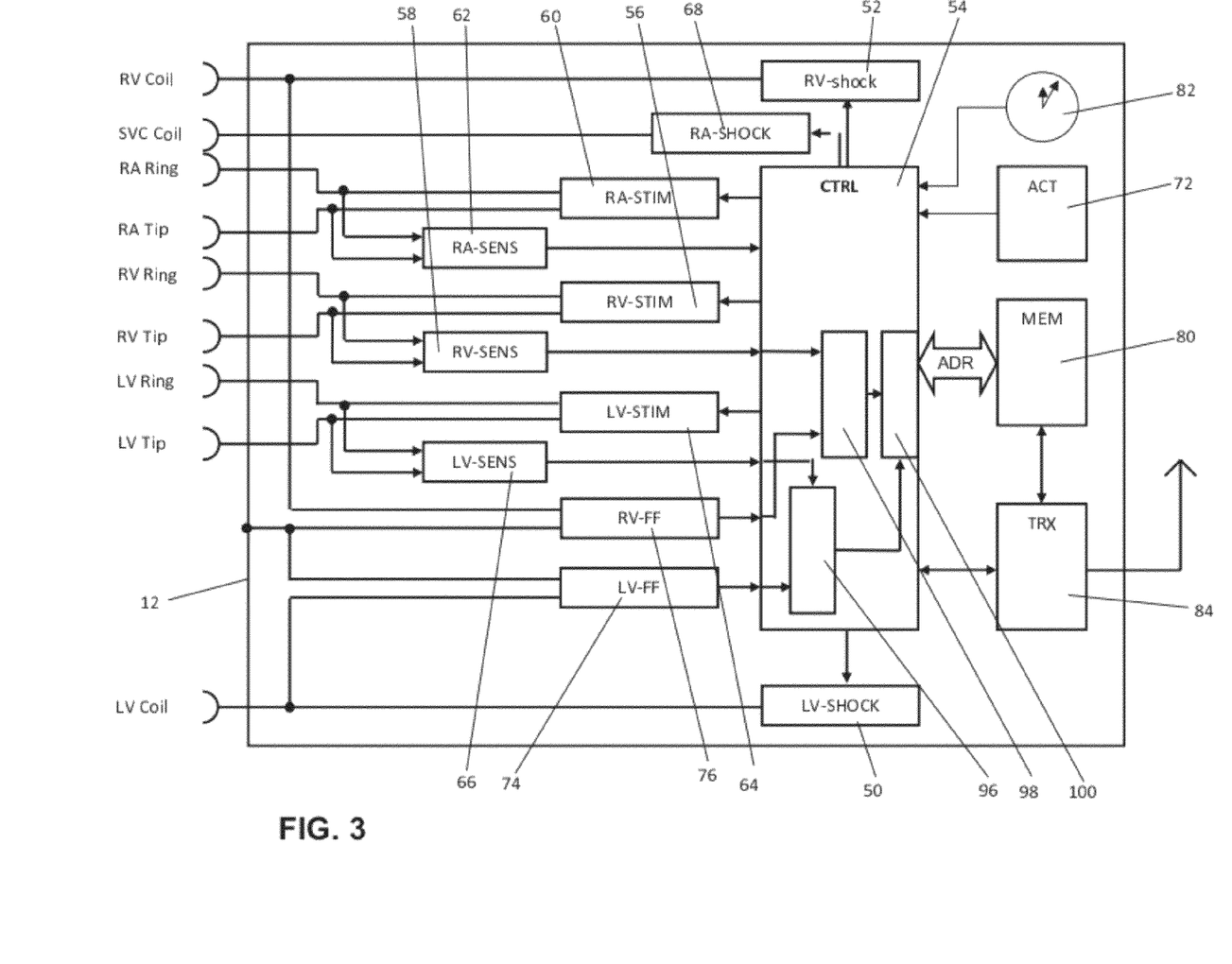
FIG. 3 depicts a schematic block diagram of some components of the heart stimulator of FIG. 1.

FIG. 2 and FIG. 3 illustrate the pacing system that includes a heart stimulator and the connected leads. The right atrial electrode lead 18 has a distal right atrial tip electrode 26 (RA-tip) at the distal end of the right atrial electrode lead 18 and a proximal right atrial ring electrode 28 (RA-ring), as well as a superior vena cava coil electrode 36 (SVC-coil) with a large surface area.

The right ventricular electrode lead 16 has a distal right ventricular tip electrode 22 (RV-tip) at the distal end of right ventricular electrode lead 16 and a proximal right ventricular ring electrode 24 (RV-ring), as well as a right ventricular defibrillation coil electrode 34 (RV-coil) with a large surface area.

Similarly, the left ventricular (LV) lead has a distal left ventricular tip electrode 30 (LV-tip) and a proximal left ventricular ring electrode 32 (LV-ring), as well as a defibrillation coil electrode 38 (LV-coil) with a large surface area. The left ventricular electrode lead 20 is designed to pass trough the coronary sinus of a heart 40. A typical electrode suitable for use with the heart stimulator 10 is the electrode lead Corox+ UP/BB by the applicant.

Each electrode and shock coil of electrode leads 16 to 20 is separately connected to an electric circuit enclosed by case 12 of heart stimulator 10. The electrodes may be connected by way of electrical contacts of a plug (not shown) at the proximal end of each electrode lead 16 to 20 and corresponding contacts (not shown) in the header 14 of heart stimulator 10.

Referring to FIG. 3, SVC shock coil 36 is connected to a right atrial shock generator 68 that is controlled by a control unit 54 of the heart stimulator 10.

Similarly, the right ventricular shock coil 34 is connected to a right ventricular shock generator 52 that is connected to the control unit 54, and left ventricular shock coil 38 is connected to a left ventricular shock generator 50 that is also connected to the control unit 54.

The right atrial tip electrode 26 and the right atrial ring electrode 28 are both connected to a right atrial stimulation pulse generator 60 and a right atrial sensing stage 62 that are internally both connected to the control unit 54.

The right atrial stimulation pulse generator 60 is adapted to generate atrial stimulation pulses of sufficient strength to cause an excitation of atrial myocardium by an electrical pulse delivered via the right atrial tip electrode 26 and the right atrial ring electrode 28. Preferably, means are provided to adapt the right atrial stimulation pulse strength to the stimulation threshold in the right atrium.

A right atrial sensing stage 58 is adapted to pick up myocardial potentials indicating an intrinsic atrial excitation that corresponds to a natural atrial contraction. By way of the right atrial sensing stage 58, it is possible to stimulate the right atrium 44 of the heart 40 in a demand mode wherein a right atrial stimulation pulse is inhibited if an intrinsic atrial event (intrinsic atrial excitation) is sensed by the right atrial sensing stage 58 prior to expiration of an atrial escape interval.

In a similar manner, the right ventricular ring electrode 24 and the right ventricular tip electrode 22 are connected to a right ventricular stimulation pulse generator 56 and to a right ventricular sensing stage 58 that in turn are connected to the control unit 54. By way of the right ventricular tip electrode 22, the right ventricular ring electrode 24, the right ventricular stimulation generator 56 and the right ventricular sensing stage 58, right ventricular stimulation pulses can be delivered in a demand mode to the right ventricle 42 of the heart 40.

In the same way, the left ventricular tip electrode 30 and the left ventricular ring electrode 32 are connected to a left ventricular stimulation pulse generator 64 and a left ventricular sensing stage 66 that are internally connected to the control unit 54 and that allow for stimulation of a left ventricle 46 of the heart 40.

Triggering and inhibition of delivery of stimulation pulses to the right atrium, the right ventricle or the left ventricle is controlled by the control unit 54, in a manner known to a person skilled in the art. The timing that schedules delivery of stimulation pulses if needed is controlled by a number of intervals that at least partly may depend on a hemodynamic demand of a patient that is sensed by means of an activity sensor 72 that is connected to the control unit 54. The activity sensor 72 allows for rate adaptive pacing wherein a pacing rate depends on a physiological demand of a patient that is sensed by a way of the activity sensor 72.

A clock 82 allows recording of events and signals in association with time stamps that enable a synchronous evaluation of signals at a later point of time.

For the purpose of composition of a far-field right ventricular electrogram (RV EGM) and a far-field left-ventricular electrogram (LV EGM), a far-field right ventricular electrogram recording unit 74 and a far-field left ventricular recording unit 76, respectively, are provided. The far-field right ventricular electrogram recording unit 74 is connected to a case electrode that is formed by at least an electrically conducting part of the case 12 of the heart stimulator 10 and to the RV coil electrode 34. The far-field left ventricular recording unit 76 is also connected to the case electrode formed by the case 12 of heart stimulator 10 and to the left ventricular coil electrode 38.

The right ventricular sensing stage 58 (for picking up near-field right ventricular electrograms) and the far-field right ventricular recording unit 74 are connected to a right ventricular activation time assessing unit 96.

The left ventricular sensing stage 66 (for generating near-field left ventricular electrogram signals) and the far-field left ventricular recording unit 76 (for picking up far-field left ventricular electrogram and generating far-field left ventricular electrogram signals) are connected to a left ventricular activation time assessing unit 98. The left ventricular sensing stage 66 and the left ventricular far-field recording unit 76 are configured to feed near-field left ventricular electrogram signals and far-field left ventricular electrogram signals, respectively, to the left ventricular activation time assessing unit 98.

The near-field electrogram in the right ventricle 42 is measured between the RV-tip electrode 22 and the RV-ring electrode 24. Preferably, the far-field electrogram in the right ventricle 38 is measured between the RV-coil electrode 34 and the device case 12. Alternatively, the far-field electrogram in the right ventricle 38 can be measured between the RV-ring electrode 24 and the device case 12.

Likewise, the near-field electrogram in the left ventricle 48 is measured between the LV-tip electrode 30 and LV-ring electrode 32. Preferably, the far-field electrogram in the left ventricle is measured between the LV-coil electrode 38 and the device case 12. Alternatively, the far-field electrogram in the left ventricle 48 can be measured between the LV-ring electrode 32 and the device case 12.

Preferably, the far-field electrograms in the right ventricle and the left ventricle are minimally filtered and have wide bandwidths, e.g., with a lower corner frequency of 4 Hz and a high corner frequency of 128 Hz. On the other hand, the near-field electrograms in the right ventricle and the left ventricle are filtered with narrower bandwidths, e.g., with a lower corner frequency of 18 Hz and a high corner frequency of 40 Hz. Accordingly, right and left far-field ventricular recording units 74 and 76 each include a band pass filter with the lower corner frequency of 4 Hz and the high corner frequency of 128 Hz. The right ventricular sensing stage 58 and the left ventricular sensing stage 66 (for picking up near-field electrograms in the right ventricle and the left ventricle) each include band pass filters with narrower bandwidths, e.g., with the lower corner frequency of 18 Hz and the high corner frequency of 40 Hz.

Simultaneous unipolar (containing far-field signals) and bipolar electrogram (EGM) recordings from a single electrode catheter have been used to assess the prematurity of local activation during ablation of focal arrhythmias (Delacretaz et al., PACE 2001; 24: 441-449). A similar concept has been recently used to measure the local activation time from EGM, which is used to explain the success or failure of antitachycardia pacing in termination of ventricular tachycardia in some patients (Lim et al., PACE 2010; 33: 549-552).

The exemplary apparatus and method illustrated herein uses a similar concept for continuous measurement of ventricular activation time (VAT). A trending analysis of VAT allows chronic monitoring of LBBB/RBBB progression and aids clinical diagnosis and early intervention.

Accordingly, the right and left ventricular activation time assessing units 96 and 98 are configured to determine a respective ventricular activation time (RV VAT or LV VAT, respectively) as further discussed below.

Figure 4:
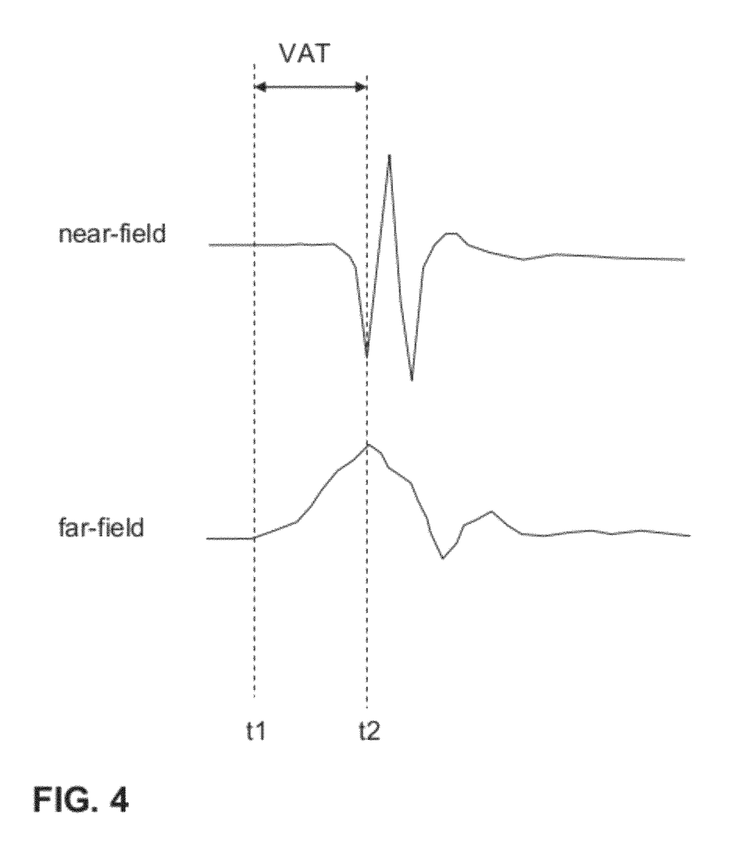
FIG. 4 is a schematic illustration of a VAT measurement.

FIG. 4 illustrates the measurement of ventricular activation time (VAT). The VAT in a ventricular chamber can be determined after each intrinsic ventricular depolarization (i.e. ventricular sense), while atrial rhythm can be either paced or sensed. The VAT in the right ventricle is derived from simultaneous measurement of near-field right ventricular electrograms and far-field right ventricular electrograms, and the VAT in the left ventricle is derived from simultaneous measurement of near-field left ventricular electrograms and far-field left ventricular electrograms. A first peak of the negative deflection on the near-field electrogram (t2) corresponds to a depolarization of the local myocardial tissue surrounding the tip electrode. An initial positive deflection on the far-field electrogram (t1) represents a far-field signal generated by the activation wavefront moving toward the recording electrode. During intrinsic ventricular conduction, this far-field activation first appears after the conduction wave completes the AV nodal conduction and enters the right and left bundle branches. Therefore, the time difference between t1 and t2 represents the time delay of ventricular conduction from the distal end of the AV junction to the recording ventricular tip electrode. In other words, the VAT in the right ventricle correlates with the right ventricular conduction time, and the VAT in left ventricle correlates with the left ventricular conduction time.

According to one typical version, the VAT is continuously measured in the right ventricle and/or the left ventricle after each ventricular sensed event. In another version, the VAT can be measured periodically or at a predefined time of the day when ventricular senses are encouraged to occur (e.g. by temporarily prolonging the device AV delay). This latter application is particularly useful for cardiac resynchronization therapy (CRT) because its normal operation usually prefers continuous ventricular capture by ventricular paces.

Preferably, the device measured VAT is stored in a device memory 80 and used for trending analysis. The time resolution of a VAT trend is preferably programmable by the user. For example, the user could interrogate the device using a programmer and show the daily, or hourly, or minute-byminute VAT (averaged over the time interval) in the right ventricle and/or the left ventricle.

The right and left ventricular activation time assessing units 96 and 98 and/or memory 80 are connected to a ventricular activation time trend analyzing unit1000. The ventricular activation time trend analyzing unit1000 is configured to analyze a trend in ventricular activation time by comparing most recently measured ventricular activation time values with a moving average of the previously measured ventricular activation time values, and to trigger a warning signal when an increase in ventricular activation time values is detected that exceeds a predefined threshold.

The trend of increasing VAT in the right ventricle suggests the development or progression of RBBB, and the trend of increasing VAT in the left ventricle suggests the development or progression of LBBB. As is known in the art, the trend of increasing VAT can be detected by comparing the most recently measured VAT value with the moving average of the previously measured VAT values, and a warning signal is generated when the increase in VAT exceeds a predefined threshold (either an absolute time interval or a percentage of previous VAT average).

Preferably, the device stored VAT trend data are also transmitted to a remote service center 94 by means of a telemetry unit 84 for trending analysis through the wired or wireless Home Monitoring network. According to one version, the transmission of VAT trend data is programmed at a predetermined time of day or predetermined time interval. According to another version, the VAT trend data are transmitted to the remote service center 94 upon device detection of a sudden increase of VAT that exceeds a predefined threshold. The threshold can be either an absolute time interval or a percentage of previous VAT average.

Figure 5:
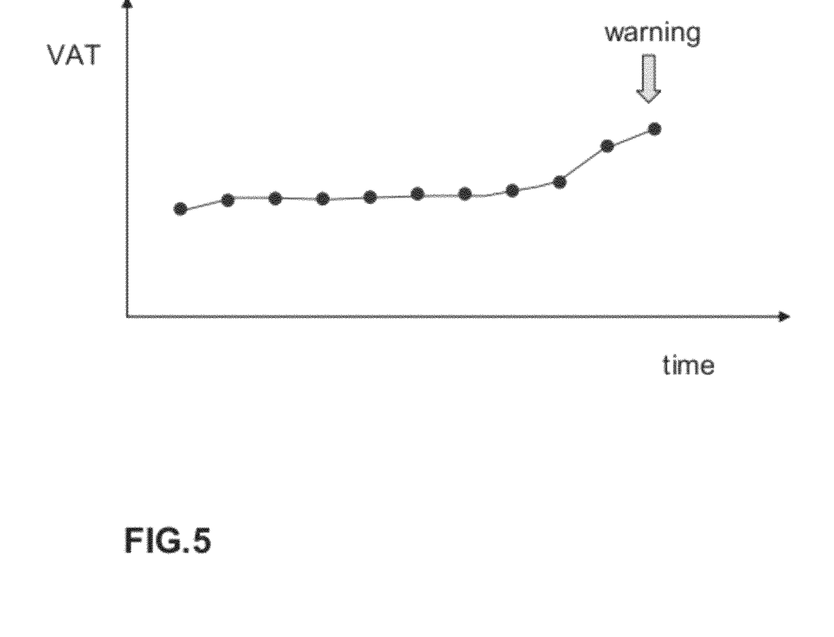
FIG. 5 is a schematic illustration of a VAT trending analysis.

As illustrated in FIG. 5, the abrupt increase of VAT in a specific ventricle may suggest the sudden development of ventricular bundle branch block, which often occurs as a result of exercise-induced myocardial ischemia. Therefore, continuous monitoring of VAT combined with a real-time alarm for increasing VAT can also provide a useful means for early detection of acute myocardial infarction and facilitate early intervention.

The exemplary apparatuses and methods disclosed herein provide a novel device feature to continuously measure the RV and LV conduction times, which could be used for long term monitoring of development and progression of LBBB/RBBB.

The exemplary apparatuses further provide a novel device feature for real-time detection of ischemia-induced ventricular conduction abnormality, thus offering a novel means for early detection and prevention of myocardial infarction.

It will be apparent to those skilled in the art that numerous modifications and variations of the described examples and versions are possible in light of the above teaching. The disclosed examples and versions are presented for purposes of illustration only. Other alternate versions may include some or all of the features disclosed herein. Therefore, it is the intent to cover all such modifications and alternate versions as may come within the true scope of this invention.

What is claimed is:

1. An implantable heart stimulator including a housing, electronic circuitry, and a ventricular activation time trend analyzing unit, wherein:
   a. the housing encloses the electronic circuitry and has an at least partially electrically conducting outer surface;
   b. the electronic circuitry is connected or can be connected to at least one electrode lead, the at least one electrode lead carrying at least two electrodes; and
   c. the electronic circuitry includes:
      i. a far-field electrogram recording unit that is electrically connected or can be connected to the at least partially electrically conducting outer surface and to a first one of the at least two electrodes;
      ii. a near-field electrogram recording unit that is electrically connected or can be connected to at least two electrodes carried by the electrode lead; and
      iii. a ventricular activation time assessing unit that is operatively connected to the far-field electrogram recording unit and the near-field electrogram recording unit, the ventricular activation time assessing unit being configured to:
         1) determine a point in time t1 of an initial positive deflection on a far-field electrogram and a point in time t2 of a first peak of the negative deflection on a near-field electrogram of a same heart cycle; and
         2) determine a time difference between points in time t1 and t2, the time difference representing a ventricular activation time;
   d. the ventricular activation time trend analyzing unit is:
      i. at least indirectly connected to the ventricular activation time assessing unit, and
      ii. configured to:
         1) analyze a trend in ventricular activation time by comparing most recently measured ventricular activation time values with a moving average of the previously measured ventricular activation time values; and
         2) trigger a warning signal when an increase in ventricular activation time values is detected that exceeds a predefined threshold.

2. The implantable heart stimulator of claim 1, wherein the first electrode is a defibrillation coil electrode.

3. The implantable heart stimulator of claim 1, wherein the electrode lead is a ventricular electrode lead.

4. The implantable heart stimulator of claim 1, wherein the near-field electrogram recording unit is a ventricular sensing unit.

5. The implantable heart stimulator of claim 1, wherein the heart stimulator is configured to continuously measure the ventricular activation time in a right ventricle and/or a left ventricle after each ventricular sensed event.

6. The implantable heart stimulator of claim 1, wherein the heart stimulator is configured to continuously measure the ventricular activation time periodically or at a predefined time of the day when ventricular senses are encouraged to occur.

7. The implantable heart stimulator of claim 1 further including a device memory and being configured to store measured ventricular activation times in the device memory in such way that the measured ventricular activation times can be used for trending analysis.

8. The implantable heart stimulator of claim 7 further including a telemetry unit and being configured to transmit stored ventricular activation time values and/or ventricular activation time trend data to a remote service center.

9. The implantable heart stimulator of claim 8 wherein the implantable heart stimulator is configured to transmit ventricular activation time trend data at a predetermined time of day or at a predetermined time interval.

10. An implantable heart stimulator including a housing, electronic circuitry, a device memory, and a telemetry unit, wherein:
    a. the housing encloses the electronic circuitry and has an at least partially electrically conducting outer surface;

b. the electronic circuitry is connected or can be connected to at least one electrode lead, the at least one electrode lead carrying at least two electrodes; and c. the electronic circuitry includes:
  i. a far-field electrogram recording unit that is electrically connected or can be connected to the at least partially electrically conducting outer surface and to a first one of the at least two electrodes;
  ii. a near-field electrogram recording unit that is electrically connected or can be connected to at least two electrodes carried by the electrode lead; and
  iii. a ventricular activation time assessing unit that is operatively connected to the far-field electrogram recording unit and the near-field electrogram recording unit, the ventricular activation time assessing unit being configured to:
    1) determine a point in time t1 of an initial positive deflection on a far-field electrogram and a point in time t2 of a first peak of the negative deflection on a near-field electrogram of a same heart cycle; and
    2) determine a time difference between points in time t1 and t2, the time difference representing a ventricular activation time;

d. the device memory is configured to store measured ventricular activation times in such a way that the measured ventricular activation times can be used for trending analysis;

e. the telemetry unit is configured to transmit ventricular activation time trend data to a remote service center:
  i. at a predetermined time of day or at a predetermined time interval, and
  ii. upon device detection of a sudden increase of ventricular activation time that exceeds a predefined threshold; and f. the predefined threshold can be either an absolute time interval or a percentage of a previous ventricular activation time average.

11. The implantable heart stimulator of claim 10, wherein the near-field electrogram recording unit is a ventricular sensing unit.

12. The implantable heart stimulator of claim 10 further including a telemetry unit configured to transmit stored ventricular activation time values and/or ventricular activation time trend data to a remote service center.

13. A method for assessing a ventricular activation time including the steps of:
  a. determining a point in time t1 of an initial positive deflection on a far-field electrogram and a point in time t2 of a first peak of the negative deflection on a near-field electrogram of a same heart cycle; and
  b. determining a time difference between points in time t1 and t2, the time difference representing the ventricular activation time;
  c. analyzing a trend in the ventricular activation time by comparing recently measured ventricular activation time values with a moving average of previously measured ventricular activation time values; and
  d. triggering a warning signal when an increase in ventricular activation time values is detected that exceeds a predefined threshold.

14. The method of claim 13 including repeated measurement of ventricular activation time in a right ventricle and/or a left ventricle activation time after each ventricular sensed event.

15. The method of claim 13 further including the step of storing measured ventricular activation time values in such way that they can be used for trending analysis.

16. The method of claim 13 further including the step of transmitting ventricular activation time trend data to a remote service center upon detection of sudden increase of ventricular activation time that exceeds a predefined threshold, the predefined threshold being either an absolute time interval or a percentage of previous ventricular activation time average.

17. A method for assessing a ventricular activation time including the steps of:
  a. determining a point in time t1 of an initial positive deflection on a far-field electrogram and a point in time t2 of a first peak of the negative deflection on a near-field electrogram of a same heart cycle;
  b. determining a time difference between points in time t1 and t2, the time difference representing the ventricular activation time; and
  c. transmitting ventricular activation time trend data to a remote service center upon detection of sudden increase of ventricular activation time that exceeds a predefined threshold, the predefined threshold being either an absolute time interval or a percentage of previous ventricular activation time average.

18. An implantable heart stimulator having:
  a. a first electrode and a second electrode;
  b. a housing for electronic circuitry, the housing having an at least partially electrically conducting outer housing surface;
  c. a ventricular activation time assessing unit configured to:
    (1) determine a point in time t1 of an initial positive deflection on a far-field electrogram and a point in time t2 of a first peak of the negative deflection on a near-field electrogram of a same heart cycle; and
    (2) determine a time difference between points in time t1 and t2, the time difference representing the ventricular activation time;
  d. a far-field electrogram recording unit connected to:
    (1) the at least partially electrically conducting outer housing surface;
    (2) the first electrode; and
    (3) the ventricular activation time assessing unit; and
  e. a near-field electrogram recording unit that is a ventricular sensing unit, the near-field electrogram recording unit being connected to:
    (1) the first and second electrodes; and
    (2) the ventricular activation time assessing unit;
  f. a ventricular activation time trend analyzing unit connected to the ventricular activation time assessing unit, the ventricular activation time trend analyzing unit being configured to:
    (1) analyze a trend in ventricular activation time by comparing most recently measured ventricular activation time values with a moving average of the previously measured ventricular activation time values; and
    (2) trigger a warning signal when an increase in ventricular activation time values exceeding a predefined threshold is detected.

19. The implantable heart stimulator of claim 18 further including a telemetry unit configured to transmit ventricular activation time values and/or ventricular activation time trend data to a remote service center.

20. The implantable heart stimulator of claim 19 wherein the telemetry unit is configured to ventricular activation time values and/or ventricular activation time trend data to the remote service center upon detection of a sudden increase in ventricular activation time that exceeds a predefined threshold.

* * * * *